United States Patent [19]
Kassan

[11] Patent Number: 5,799,654
[45] Date of Patent: Sep. 1, 1998

[54] DIAPER CHANGING AID

[76] Inventor: Lawrence Kassan, 46 Partridge La., Cherry Hill, N.J. 08003

[21] Appl. No.: 821,212

[22] Filed: Mar. 20, 1997

[51] Int. Cl.$^6$ .................................................. A61B 19/00
[52] U.S. Cl. ........................... 128/869; 128/876; 128/882
[58] Field of Search ........................... 128/845, 846, 128/869, 874, 875, 876, 878, 879, 882; 602/23, 28; 5/650, 651

[56] References Cited

U.S. PATENT DOCUMENTS

| | | | |
|---|---|---|---|
| 4,046,143 | 9/1977 | Bell | 128/882 |
| 4,173,974 | 11/1979 | Belliveau | 128/882 |
| 4,620,535 | 11/1986 | Nesbitt | 128/869 |
| 5,437,402 | 8/1995 | Ring | 128/882 |

*Primary Examiner*—Michael A. Brown

[57] ABSTRACT

A new Diaper Changing Aid for providing a device that would gently restrain the ankles of a child in a slightly separated position during a diaper change. The inventive device includes a restraining member adapted for holding the ankles of a child in spaced relation, and a handle detachably pivotally coupled to the restraining member so as to enable a caregiver to hold and lift the ankles of the child with one hand during the diaper change. Entertaining attachments are attachable to the handle for providing a source of entertainment and distraction for the child during the diaper changing process.

15 Claims, 3 Drawing Sheets

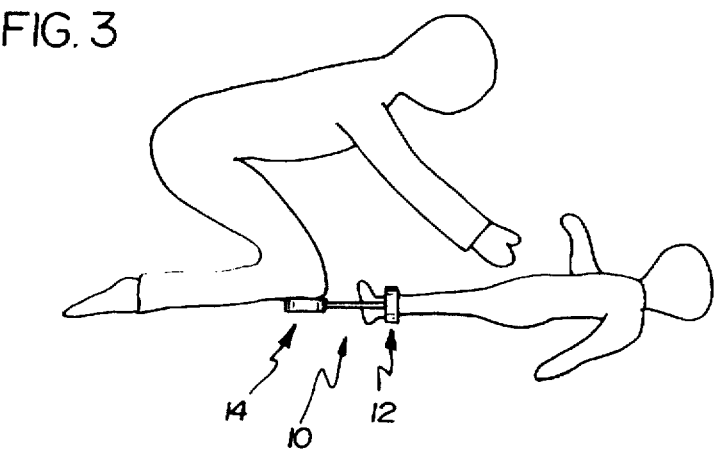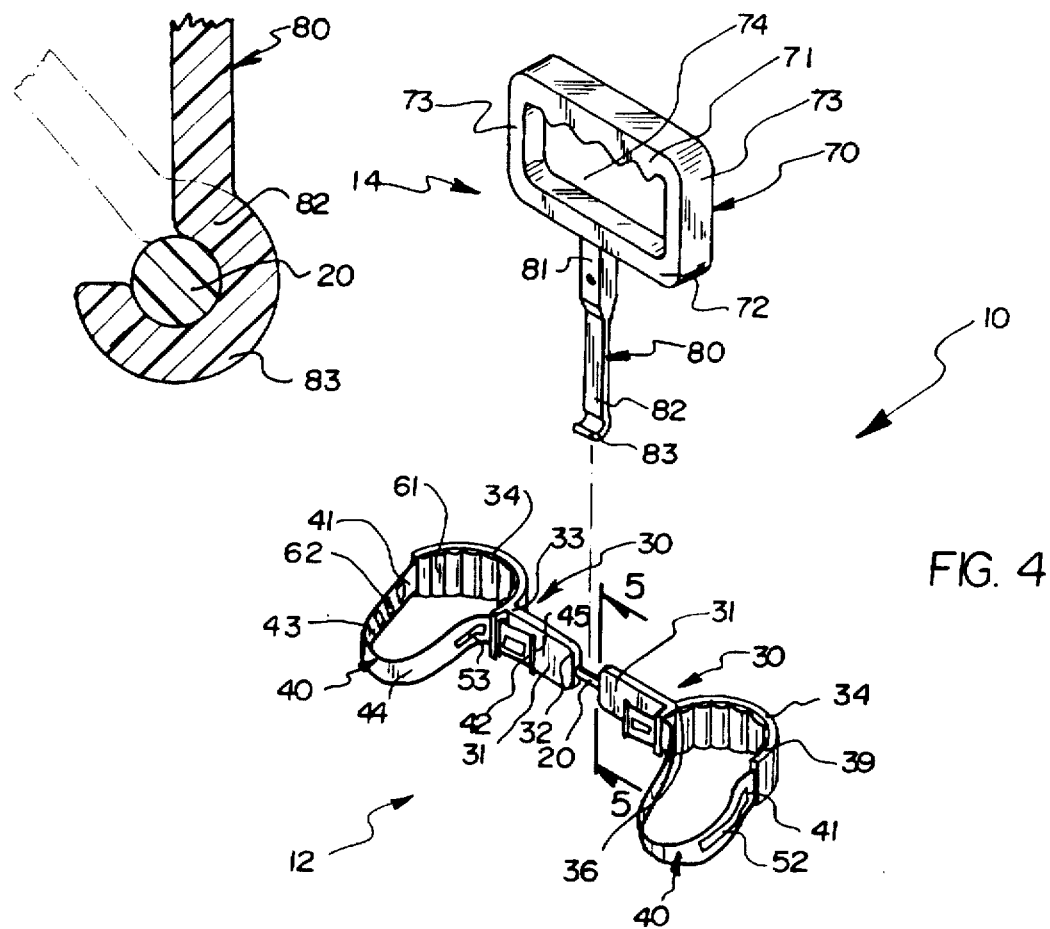

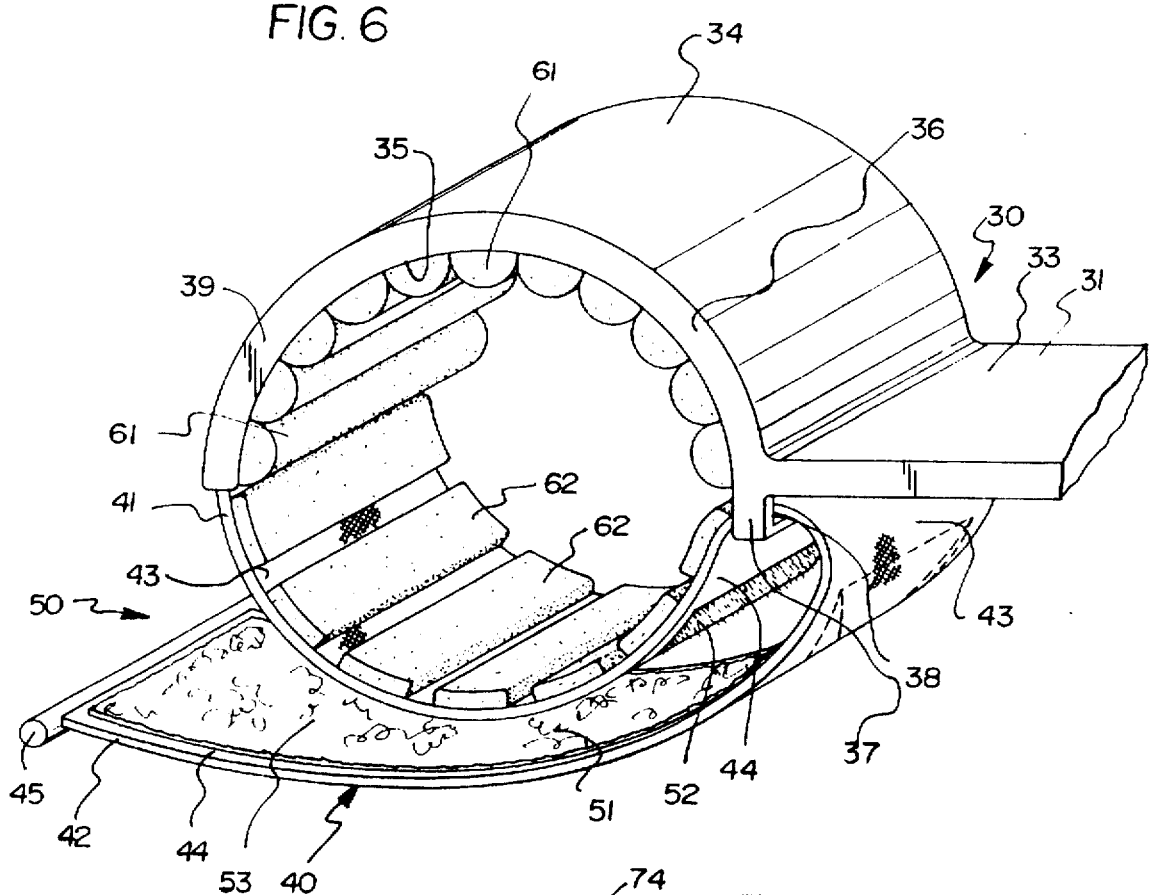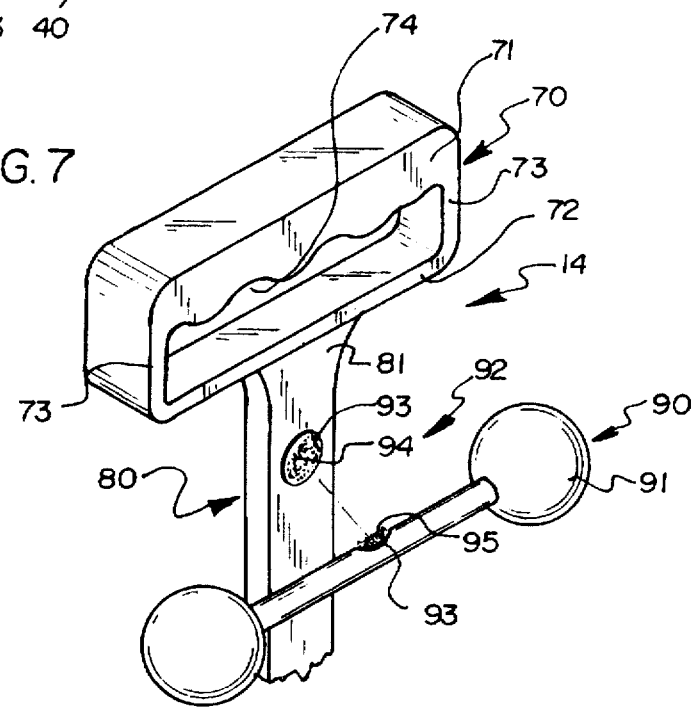

DIAPER CHANGING AID

BACKGROUND OF THE INVENTION

1. Field of the Invention

The present invention relates to ankle restraint devices and more particularly pertains to a new Diaper Changing Aid for providing a device that would gently restrain the ankles of a child in a slightly separated position during a diaper change.

2. Description of the Prior Art

The use of ankle restraint devices is known in the prior art. More specifically, ankle restraint devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art ankle restraint devices include U.S. Pat. Nos. 5,437,402; 4,024,736; D343,510; 4,205,669; 4,781,373; and 4,728,103.

While these devices fulfill their respective, particular objectives and requirements, the aforementioned patents do not disclose a new Diaper Changing Aid. The inventive device includes a restraining member adapted for holding the ankles of a child in spaced relation, and a handle detachably pivotally coupled to the restraining member so as to enable a caregiver to hold and lift the ankles of the child with one hand during a diaper change. Entertaining attachments are attachable to the handle for providing a source of entertainment and distraction for the child during the diaper changing process.

In these respects, the Diaper Changing Aid according to the present invention substantially departs from the conventional concepts and designs of the prior art, and in so doing provides an apparatus primarily developed for the purpose of providing a device that would gently restrain the ankles of a child in a slightly separated position during a diaper change.

SUMMARY OF THE INVENTION

In view of the foregoing disadvantages inherent in the known types of ankle restraint devices now present in the prior art, the present invention provides a new Diaper Changing Aid construction wherein the same can be utilized for providing a device that would gently restrain the ankles of a child in a slightly separated position during a diaper change.

The general purpose of the present invention, which will be described subsequently in greater detail, is to provide a new Diaper Changing Aid apparatus and method which has many of the advantages of the ankle restraint devices mentioned heretofore and many novel features that result in a new Diaper Changing Aid which is not anticipated, rendered obvious, suggested, or even implied by any of the prior art ankle restraint devices, either alone or in any combination thereof.

To attain this, the present invention generally comprises a restraining member adapted for holding the ankles of a child in spaced relation, and a handle detachably pivotally coupled to the restraining member so as to enable a caregiver to hold and lift the ankles of the child with one hand during a diaper change. Entertaining attachments are attachable to the handle for providing a source of entertainment and distraction for the child during the diaper changing process.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Diaper Changing Aid apparatus and method which has many of the advantages of the ankle restraint devices mentioned heretofore and many novel features that result in a new Diaper Changing Aid which is not anticipated, rendered obvious, suggested, or even implied by any of the prior art ankle restraint devices, either alone or in any combination thereof.

It is another object of the present invention to provide a new Diaper Changing Aid which may be easily and efficiently manufactured and marketed.

It is a further object of the present invention to provide a new Diaper Changing Aid which is of a durable and reliable construction.

An even further object of the present invention is to provide a new Diaper Changing Aid which is susceptible of a low cost of manufacture with regard to both materials and labor, and which accordingly is then susceptible of low prices of sale to the consuming public, thereby making such Diaper Changing Aid economically available to the buying public.

Still yet another object of the present invention is to provide a new Diaper Changing Aid which provides in the apparatuses and methods of the prior art some of the advantages thereof, while simultaneously overcoming some of the disadvantages normally associated therewith.

Still another object of the present invention is to provide a new Diaper Changing Aid for providing a device that would gently restrain the ankles of a child in a slightly separated position during a diaper change.

Yet another object of the present invention is to provide a new Diaper Changing Aid which includes a restraining

3 member adapted for holding the ankles of a child in spaced relation, and a handle detachably pivotally coupled to the restraining member so as to enable a caregiver to hold and lift the ankles of the child with one hand during a diaper change. Entertaining attachments are attachable to the handle for providing a source of entertainment and distraction for the child during the diaper changing process.

Still yet another object of the present invention is to provide a new Diaper Changing Aid that would allow a caregiver to hold and lift the ankles of a child with one hand during a diaper change. Accordingly, the present invention provides the caregiver with easier access to the child and provides the caregiver with a free hand for removing the used diaper, cleaning, applying lotion or powder, and positioning the new diaper.

Even still another object of the present invention is to provide a new Diaper Changing Aid that increases the safety of a diaper change by restraining a child from flailing and struggling which could result in injury to the child when a caregiver attempts to restrain the child simply by hand during the diaper change. Furthermore, the present invention increases the convenience of the diaper change by enabling the caregiver to complete the diaper change faster and more easily, thus making it a much less frustrating task for both the child and the caregiver.

Even still another object of the present invention is to provide a new Diaper Changing Aid that would allow for optimal positioning of a child for thorough examination, cleaning, and ointment/medication application.

Even still another object of the present invention is to provide a new Diaper Changing Aid that would be compact, portable, and easy to store; would easily fit into a diaper or tote bag; and would be completely washable.

Even still another object of the present invention is to provide a new Diaper Changing Aid that could be used in day care centers or other institutions that provide care to children; and could be used in medical settings such as hospitals and pediatrician's offices as an aid in infant and toddler examinations and medical procedures.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is an additional illustration of the present invention in use.

FIG. 4 is an isometric illustration of the present invention.

FIG. 5 is a cross sectional view taken along line 5—5 of FIG. 4.

FIG. 6 is an illustration of one end of the restraining member of the present invention.

FIG. 7 is an illustration of the handle of the present invention and an entertaining attachment attached thereto.

DESCRIPTION OF THE PREFERRED EMBODIMENT

Figure 1:
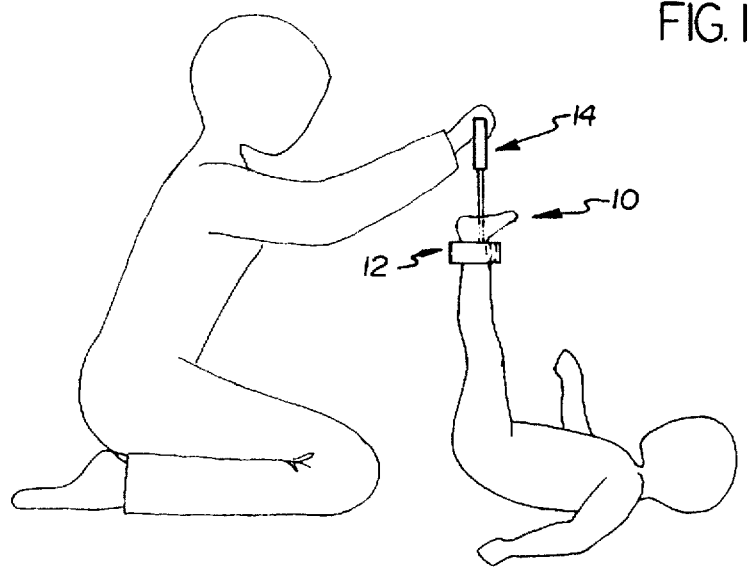
FIG. 1 is an illustration of a new Diaper Changing Aid in use according to the present invention.

With reference now to the drawings, and in particular to FIGS. 1 through 7 thereof, a new Diaper Changing Aid embodying the principles and concepts of the present invention and generally designated by the reference numeral 10 will be described.

More specifically, it will be noted that the Diaper Changing Aid 10 comprises a restraining member 12 adapted for holding the ankles of a child in spaced relation, and a handle 14 detachably pivotally coupled to the restraining member 12 so as to enable a caregiver to hold and lift the ankles of the child with one hand during a diaper change. Entertaining attachments 90 are attachable to the handle 14 for providing a source of entertainment and distraction for the child during the diaper changing process.

Figure 2:
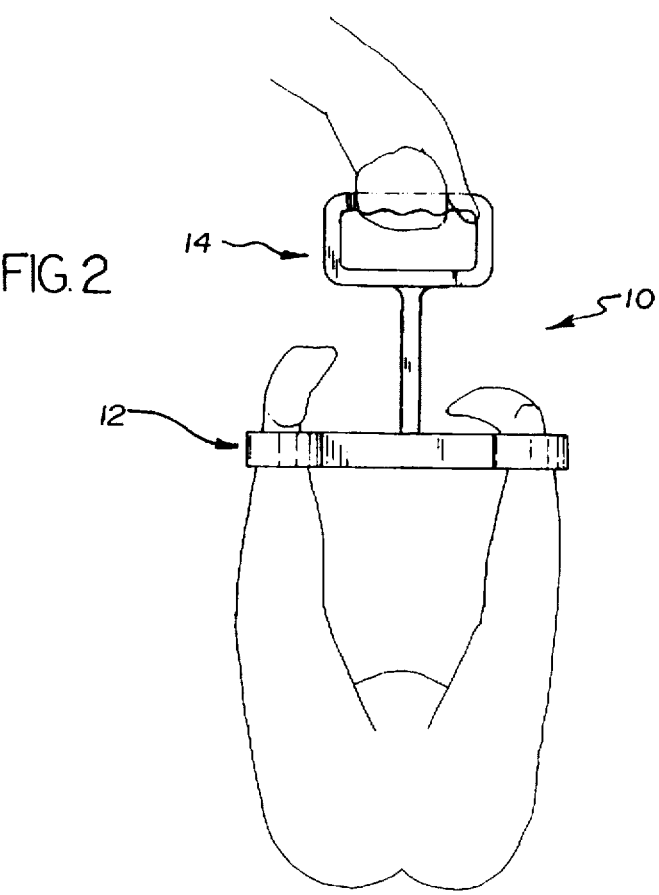
FIG. 2 is an additional illustration of the present invention in use.

As best illustrated in FIGS. 1 through 3, it can be shown that the present invention may be used for gently restraining the ankles of a child in a slightly separated position during a diaper change. Accordingly, the present invention enables a caregiver to hold and lift the ankles of the child with one hand during the diaper change (FIGS. 1 and 2). Alternatively, the caregiver may place his or her knee on the handle 14 so as to free both hands for removing a used diaper and positioning a new diaper (FIG. 3).

As best illustrated in FIGS. 4 through 6, it can be shown that the restraining member 12 comprises a center connecting rod 20, a pair of arms 30 oppositely extending from the center connecting rod 20, and a strap 40 attached to each of the pair of arms 30, wherein the ankles of the child are secured in spaced relation to the pair of arms 30 by the straps 40. In an illustrative embodiment, the restraining member 12 measures about 8 inches in length such the ankles of the child are separable by about 6 inches.

Each of the pair of arms 30 includes an extension portion 31 and a C-shaped portion 34. The extension portion 31 and the C-shaped portion 34 are substantially rigid. The extension portion 31 includes an inner end 32 and an outer end 33 and the C-shaped portion 34 includes an inner leg 36 and an outer leg 39. The inner end 32 of the extension portion 31 is joined to one end of the center connecting rod 20 and the inner leg 36 of the C-shaped portion 34 is joined to the outer end 33 of the extension portion 31. The inner leg 36 extends slightly beyond the extension portion 31 so as to form a tab 37 wherein the tab 37 has a slot 38 therein.

The strap 40 has a first end 41 and a second end 42 and has an inner surface 43 and an outer surface 44. The first end 41 of the strap 40 is joined to the outer leg 39 of the C-shaped portion 34 of each of the pair of arms 30. The second end 42 of the strap 40 is slidable through the slot 38 provided in the tab 37. A bar 45 having a length slightly longer than that of the slot 38 is joined to the second end 42 of the strap 40. As such, the bar 45 prevents the second end 42 of the strap 40 from easily passing through the slot 38.

A releasably adjustable fastening means 50 is provided for releasably and adjustably fastening the strap 40 snugly against the ankles of the child. The releasably adjustable fastening means 50 comprises a hook and loop fastener 51 having a hook portion 52 provided on the outer surface 44 of the strap 40 adjacent the first end 41 thereof and having a loop portion 53 provided on the outer surface 44 of the strap 40 adjacent the second end 42 thereof. As such, the strap 40 is pulled through the slot 38, looped around the tab 37, and releasably adjustably fastened to itself such that the second end 42 of the strap 40 is fastened adjacent the first end 41 of the strap 40. The bar 45 provided at the second end 42 of the strap 40 facilitates gripping of the strap 40 for fastening and releasing thereof.

The C-shaped portion 34 of each of the pair of arms 30 and the strap 40 are both padded for a comfortable fit around the ankles of the child. As such, a first cushioning member 61 is provided on an inner surface 35 of the C-shaped portion 34 of each of the pair of arms 30 and a second cushioning member 62 is provided on the inner surface 43 of the strap 40 adjacent the first end 41 thereof. The cushioning members 61 and 62 easily conform to the ankles of the child and allow the strap 40 to be snugly adjusted thereagainst.

As best illustrated in FIGS. 4 through 6, it can be shown that the handle 14 is substantially rigid and includes a gripping portion 70 and a shank portion 80 extending downward from the gripping portion 70. The gripping portion 70 of the handle 14 comprises an upper member 71, a lower member 72, and a pair of spaced side members 73 interconnecting the upper member 71 and the lower member 72 in spaced relation so as to define an opening 74 adapted for receiving the hand of the user. The upper member 71 of the gripping portion 70 is formed for ease of gripping thereof in one hand.

The shank portion 80 of the handle 14 has an upper end 81 and a lower end 82 wherein the lower end 82 of the shank portion 80 terminates with a hook 83. The upper end 81 of the shank portion 80 is joined to the lower member 72 of the gripping portion 70. The lower end 82 of the shank portion 80 is detachably pivotally coupled to the restraining member 12 wherein the hook 83 is snap-fittingly coupled to the center connecting rod 20 of the restraining member 12. As such, the handle 14 is free to pivot about the center connecting rod 20 relative to the restraining member 12 and may be easily uncoupled. In an illustrative embodiment, the handle measures about 12 inches in length.

The entertaining attachments 90 are releasably attachable to the handle 14. The entertaining attachments 90 include a rattle 91, spinners (not shown), bells (not shown), and fluid-filled compartments with stars, glitter, or other shapes suspended therein (not shown). The entertaining attachments 90 are designed so as to be colorful, pleasing, and attractive to the child. A releasable fastener 92 is provided for releasably fastening the entertaining attachments 90 to the shank portion 80 of the handle 14. The releasable fastener 92 comprises a hook and loop fastener 93 including a hook portion 94 provided on the shank portion 80 of the handle 14 and a loop portion 95 provided on the entertaining attachments 90.

In use, the handle 14 is pivotally coupled to the restraining member 12 wherein the hook 83 of the shank portion 80 is snap-fittingly coupled to the center connecting rod 20 of the restraining member 12. As such, the handle 14 is free to pivot about the center connecting rod 20 relative to the pair of arms 30.

The first ankle of the child is placed in abutting engagement with the C-shaped portion 34 of a first of the pair of arms 30 of the restraining member 12. The strap 40 is pulled through the slot 38 and looped back around the tab 37. The cushioning members 61 and 62 easily conform to the ankle of the child and allow the strap 40 to be snugly adjusted thereagainst. The strap 40 is releasably adjustably fastened to itself such that the second end 42 of the strap 40 is fastened adjacent the first end 41 of the strap 40 with the hook and loop fastener 51. Thereafter, the second ankle of the child is placed in abutting engagement with the C-shaped portion 34 of a second of the pair of arms 30 of the restraining member 12 and secured therein in a similar manner.

As such, the ankles of the child are gently restrained in a slightly separated position. The caregiver can then use the handle 14 and the restraining member 12 to hold and lift the ankles of the child with one hand. Alternatively, the caregiver may place his or her knee on the handle 14 so as to free both hands. When used during a diaper change, the present invention allows the caregiver to hold and lift the ankles of the child with one hand so as to provide the caregiver with a free hand for removing the used diaper, cleaning and applying lotion or powder to the child, and positioning the new diaper. Additionally, the present invention may be used in medical settings such as hospitals and pediatrician's offices as an aid in infant and toddler examinations and medical procedures. When not in use, the handle 14 may be detached from the restraining member 12 so as to facilitate storage thereof in, for example, a diaper or tote bag.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An apparatus for restraining and elevating the ankles of a child in spaced relation, comprising:
    a restraining member adapted for holding the ankles of the child in a fixed spaced relation to each other; and
    a handle detachably pivotally coupled to said restraining member, said restraining member and said handle enabling a user to hold and lift the ankles of the child with one hand;
    wherein said restraining member comprises:
        a center connecting rod,
        a pair of arms extending outwardly from said center connecting rod, said arms being in a fixed position relative to said center connecting rod; and
        a strap attached to each of said pair of arms, wherein the ankles of the child are securable in spaced relation to said pair of arms by said straps.

2. The apparatus of claim 1, further comprising:
    a releasably adjustable fastening means for releasably and adjustably fastening said strap against the ankles of the child.

3. The apparatus of claim 2, wherein said releasably adjustable fastening means comprises:

a hook and loop fastener having a hook portion provided on said outer surface of said strap adjacent said first end thereof and having a loop portion provided on said outer surface of said strap adjacent said second end thereof, said strap releasably adjustably fastenable to itself whereby said second end of said strap is releasably adjustably fastened adjacent said first end of said strap.

4. The apparatus of claim 1, wherein said handle includes a gripping portion and a shank portion extending downward from said gripping portion, said shank portion having a lower end detachably pivotally coupled to said restraining member.

5. The apparatus of claim 4, wherein said gripping portion of said handle comprises:

an upper member adapted for gripping thereof in one hand, a lower member, and a pair of spaced side members interconnecting said upper member and said lower member in spaced relation so as to define an opening adapted for receiving the hand of said user.

6. The apparatus of claim 1, further comprising:

an entertaining attachment releasably attachable to said handle.

7. An apparatus for restraining and elevating the ankles of a child in spaced relation, comprising:

a restraining member adapted for holding the ankles of the child in spaced relation;

a handle detachably pivotally coupled to said restraining member, said restraining member and said handle enabling a user to hold and lift the ankles of the child with one hand;

a center connecting rod;

a pair of arms oppositely extending from said center connecting rod;

a strap attached to each of said pair of arms, wherein the ankles of the child are securable in spaced relation to said pair of arms by said straps;

an extension portion having an inner end and an outer end, said inner end of said extension portion joined to one end of said center connecting rod; and a C-shaped portion having an inner leg and an outer leg, said inner leg of said C-shaped portion joined to said outer end of said extension portion, said inner leg extending beyond said extension portion so as to form a tab, and said tab having a slot therein.

8. The apparatus of claim 7, wherein said strap has a first end and a second end and has an inner surface and an outer surface, said first end of said strap joined to said outer leg of said C-shaped portion of each of said pair of arms, said second end of said strap slidable through said slot in said tab.

9. The apparatus of claim 8, further comprising:

a bar provided at said second end of said strap, said bar having a length greater than that of said slot whereby said bar hinders passage of said second end of said strap through said slot.

10. The apparatus of claim 8, further comprising:

a releasably adjustable fastening means for releasably and adjustably fastening said strap against the ankles of the child.

11. The apparatus of claim 10, wherein said releasably adjustable fastening means comprises:

a hook and loop fastener having a hook portion provided on said outer surface of said strap adjacent said first end thereof and having a loop portion provided on said outer surface of said strap adjacent said second end thereof, said strap releasably adjustably fastenable to itself whereby said second end of said strap is releasably adjustably fastened adjacent said first end of said strap.

12. The apparatus of claim 8, further comprising:

a first cushioning member provided on an inner surface of said C-shaped portion of each of said pair of arms, and a second cushioning member provided on said inner surface of said strap adjacent said first end thereof.

13. The apparatus of claim 7, wherein said handle includes a gripping portion and a shank portion extending downward from said gripping portion, said shank portion having a lower end detachably pivotally coupled to said restraining member.

14. The apparatus of claim 13, wherein said gripping portion of said handle comprises:

an upper member adapted for gripping thereof in one hand, a lower member, and a pair of spaced side members interconnecting said upper member and said lower member in spaced relation so as to define an opening adapted for receiving the hand of said user.

15. The apparatus of claim 7, further comprising:

an entertaining attachment releasably attachable to said handle.

* * * * *